(12) United States Patent
York (10) Patent No.: US 8,630,872 B2
(45) Date of Patent: Jan. 14, 2014

(54) COMPETITION DRIVEN HEALTH MANAGEMENT

(75) Inventor: Chris York, San Francisco, CA (US)

(73) Assignee: Keas, Inc., San Francisco, CA (US)

( * ) Notice: Subject to any disclaimer, the term of this patent is extended or adjusted under 35 U.S.C. 154(b) by 0 days.

(21) Appl. No.: 13/365,119

(22) Filed: Feb. 2, 2012

(65) Prior Publication Data

US 2012/0303377 A1   Nov. 29, 2012

Related U.S. Application Data

(60) Provisional application No. 61/438,930, filed on Feb. 2, 2011.

(51) Int. Cl.
*G06Q 10/00*     (2012.01)
*G06Q 50/00*     (2012.01)

(52) U.S. Cl.
USPC .................................. 705/2; 705/3; 600/300

(58) Field of Classification Search
USPC .......................................... 705/2, 3; 600/300
See application file for complete search history.

(56) References Cited

U.S. PATENT DOCUMENTS 8,374,888 B2 *   2/2013   Earles et al. ...................... 705/2
2012/0179489 A1 *   7/2012   Gupta ............................. 705/3

* cited by examiner

*Primary Examiner* — Michelle Le
(74) *Attorney, Agent, or Firm* — Lewis Roca Rothgerber LLP (57) ABSTRACT

An application offers personalized content, such as health care plans, health actions, and interactive games, to a user. Based on such health data provided by a user, the health management application may provide content, such as health information or health care plans, that is tailored to the current health status or condition of the user. In some instances, a user may request to participate in a particular health action or task. The health management application may recommend personalized tasks or actions for the user to complete to promote and improve health. Following partial or successful completion of a chosen health action, a user may earn points or rewards that may be redeemable for various prizes. A user may also earn points by completing an educational or informational task such as quizzes, questionnaires, or surveys. Points may also be earned by participating in or playing a game.

20 Claims, 9 Drawing Sheets

COMPETITION DRIVEN HEALTH MANAGEMENT

BACKGROUND

Field of the Invention

The present invention generally concerns health management. More particularly, the present invention relates to a health management application that allows a user or team of users that are a part of a social network to earn rewards and prizes for completing personalized health-related actions and tasks.

DETAILED DESCRIPTION

Embodiments of the present invention provide an application for offering personalized content, such as health care plans, health actions, and interactive games, to a user. A user may provide health data to a health management application. Based on such health data, the health management application may provide content, such as health information or health care plans, that is tailored to the current health status or condition of the user. In some instances, a user may request to participate in a particular health action or task. The health management application may recommend personalized tasks or actions (i.e., based on the user health data) for the user to complete to promote and improve health. Following partial or successful completion of a chosen health action, a user may earn points or rewards that may be redeemable for various prizes. A user may also earn points by completing an educational or informational task such as quizzes, questionnaires, or surveys. Points may also be earned by participating in or playing a game.

In conjunction with providing personalized health content and information, the health management application may include a social networking or social support component that allows a user to interact and connect with other users. Users may interact and connect with each other in various ways known in the art such as creating a profile, inviting friendships or connections, exchanging messages, chatting, sharing information, posting status updates, giving and receiving feedback, joining common interest groups, and the like. In one embodiment, a user joins or forms a team of users that are in the same social network or community. The team may share a common health-related interest or goal such as a team of users trying to lose weight or a team of users all suffering from a particular ailment such as diabetes or arthritis. The health management application may serve as a social support network for team members of a community sharing a common interest as users are able to easily and instantaneously communicate, coach, encourage, support, and praise one another while, for example, trying to achieve a particular health goal.

An individual user or team member may receive or earn points for completing a particular health-related task or action. A health action may be recommended by the health management application or the user may choose from a list of available health actions. The points earned by each individual team member may be tracked, incremented, and/or summed together for a total team score. The team (and/or individual user) may earn a reward or prize upon achieving a particular score and may compete against other teams for various prizes. A team member may thus work individually or in combination with other team members of the same social network or community to complete health actions and earn points redeemable for prizes.

By completing a health action that helps to maintain a healthy lifestyle, a user may improve current health status while earning rewards. A team of users sharing a common interest or goal may also promote increased adherence to a healthy lifestyle as each team member may feel a social or team obligation to complete various health actions and remain at a consistent health status and/or reward level status with other team members. A user may thus be held accountable for activity or inactivity since the profile of the user and any on-line activities of the user may be visible to other team members and users in the social network or community.

In some embodiments, the present health management application may be implemented by one or more processors that execute instructions stored in one or more memory mediums. The executed code may result in the processor(s) generating and providing one or more graphical interfaces. FIGS. 2-8 illustrate examples of interfaces used to implement embodiments of the present invention. An exemplary system and method for implementing the present health management application is described in the context of FIGS. 1 and 9, respectively.

Figure 1:
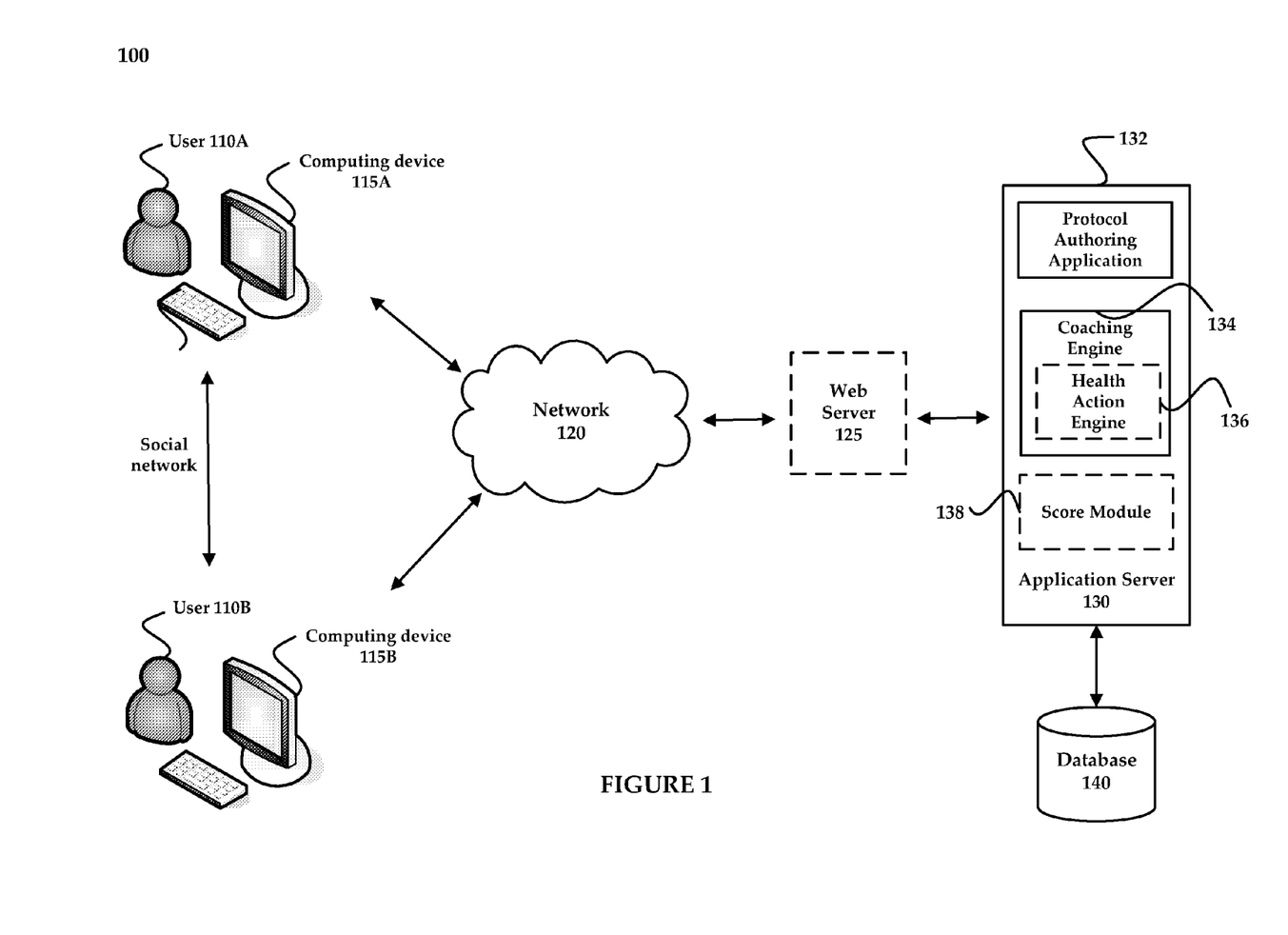
FIG. 1 illustrates a system for authoring a protocol for processing user health data and generating personalized content.

FIG. 1 illustrates a system 100 for authoring a protocol for processing user health data and generating personalized content. The system of FIG. 1 includes user (110A, 110B), computing device (115A, 115B), network 120, optional web server 125, application server 130, and database 140.

A user (110A, 110B) may access the health management application using any computing device (115A, 115B) (e.g., workstation, server, lap top computer, mobile device, etc.) capable of accessing information over a communication network 120 known in the art. In one embodiment, a user 110A may be an anonymous user of the health management application. An anonymous user may be one who has not subscribed, registered, or created an account with the health management application.

User 110A may register (i.e., create an account) with the health management application. User 110A at computing device 115A may perform a login with a service provided by coaching engine 134 and receive interface data as a browser application content page. User 110A of the health management system may be required to provide registration information and health data. Health data may include any data related to the mental or physical health of the user such as medications, health goals, eating habits, medical history, family history, allergies, and current health condition(s). The user 110A may also provide background data such as user attributes (e.g., age, weight, birthday, gender, height) and vital signs (e.g., temperature, heart rate, pulse, respiratory rate, blood pressure). The user 110A may also provide lifestyle information such as health interests, nutritional information, alcohol or tobacco consumption, and physical activities. User health data may be stored in a data store 140 that communicates with application server 130 of the network.

The application server 130 may host the health management application. Application server 130 may be implemented in a general computing device that communicates with data store 140 and optional web server 125. The application server 130 as illustrated in FIG. 1 includes protocol authoring application 132 and coaching engine 134. Protocol authoring application 132 may be executed by a processor to provide interface data concerning a graphical interface to a computing device (e.g., computing device 115A). This interface data may then be executed and rendered as an interface by computing device 115A such as a web browser or Java Virtual Machine. The interface generated from the interface data can be used by computing device 115A for authoring a protocol related to health coaching. The application server 130 may also include a coaching engine 134 that is executable by a processor to administer a user health coach protocol. A more detailed discussion of a protocol for providing user health coaching and an authoring protocol may be found in APPENDIX A of the present application.

The application server 130 may also include various modules or engines stored in memory and executable by a processor at the application server or user computing device to implement the present invention. The application server 130, for example, may include health action engine 136 and score module 138. The health action engine 136 may be executed by a processor to receive user health data, recommend a health action to a user, and receive confirmation from a user that a recommended health action has been partially or successfully completed. Score module 138 may be executed by a processor to track, manage, and increment a score associated with user 110A. Score module 138 may also adjust a score based on the activity or inactivity of user 110A.

Figure 2:
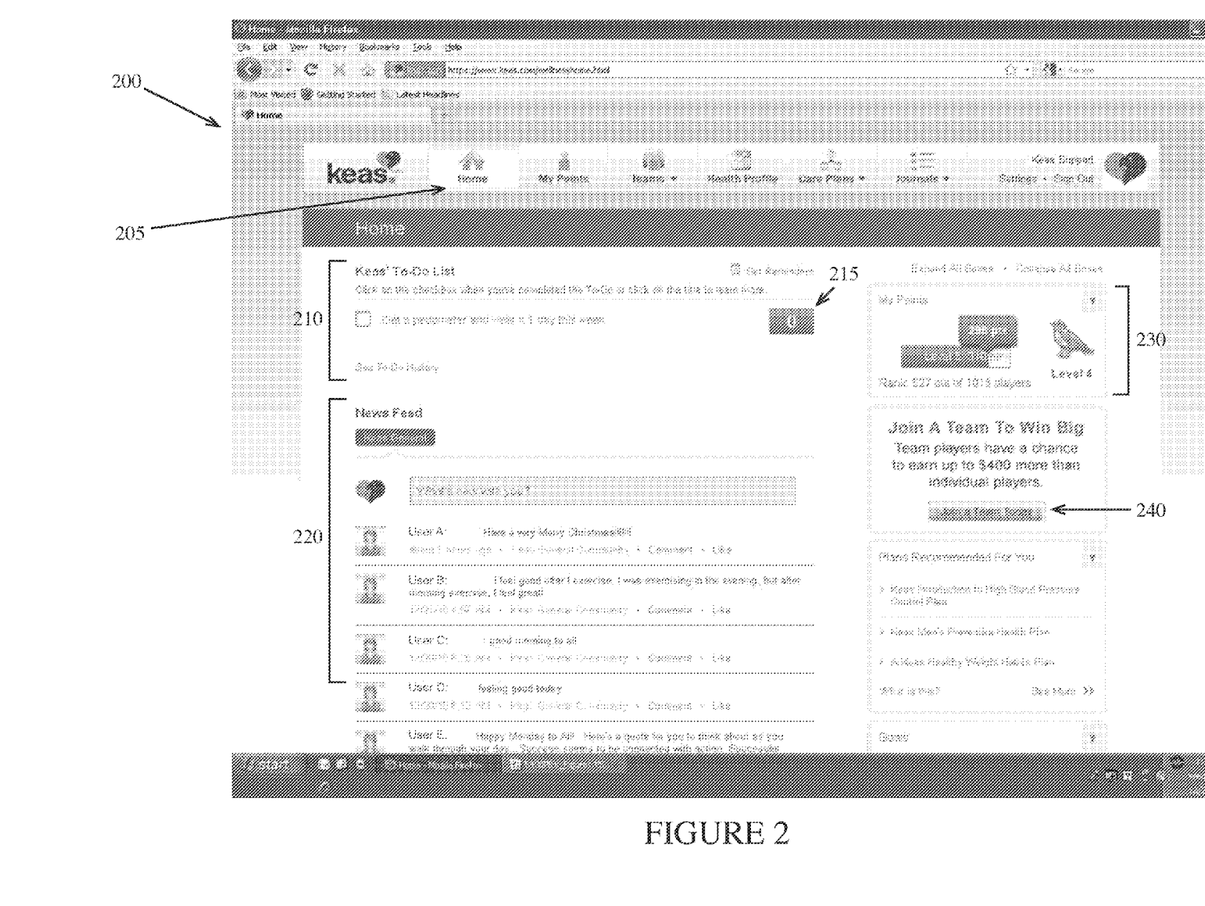
FIG. 2 illustrates an interface for allowing a user to interact with various components of a health management application.

FIG. 2 illustrates an interface for allowing a user to interact with various components of a health management application. Interface 200 includes various menus or tabs, such as "Home," "My Points," and "Teams," located at the upper portion of the interface. FIG. 2 shows interface 200 with the "Home" menu 205 selected. The "Home" menu 205 may include several components for user interaction such as a "To-Do List" 210, health action points 215, News Feed 220, points summary 230, and an invitation to join a team 240.

The "To-Do List" 210 in FIG. 2 shows one health action or activity ("Get a pedometer and wear 1 day this week") for user 110A to complete. As shown, user 110A has not yet completed the activity and the health action points 215 associated with the activity remains at zero. If user 110A completes the health action, user 110A may check the box next to the health action (or otherwise indicate that the health action has been completed) and the health action points 215 may be updated or incremented based on successful completion. In one embodiment, the health management application recommends or lists one or more health actions for user 110A to complete based on health data previously provided by user 110A. As such, the health actions are tailored to the health condition or status of the user 110A. For example, if user 110A has indicated "weight loss" as a primary health goal and user 110A has "high cholesterol," health management application may recommend via the "To-Do List" 210 that the user "Skip red meat this week" or "exercise for 30 minutes today." The health management application may also provide reminders to user 110A to complete actions on the "To-Do List" 210. Reminders may be provided to user 110A via electronic mail (e-mail), SMS text message, instant messenger, chat, or any other available communication medium. "News Feed" 220, points summary 230, and the invitation to join a team 240 are discussed in more detail below with respect to FIGS. 3, 4, and 5, respectively.

Figure 3:
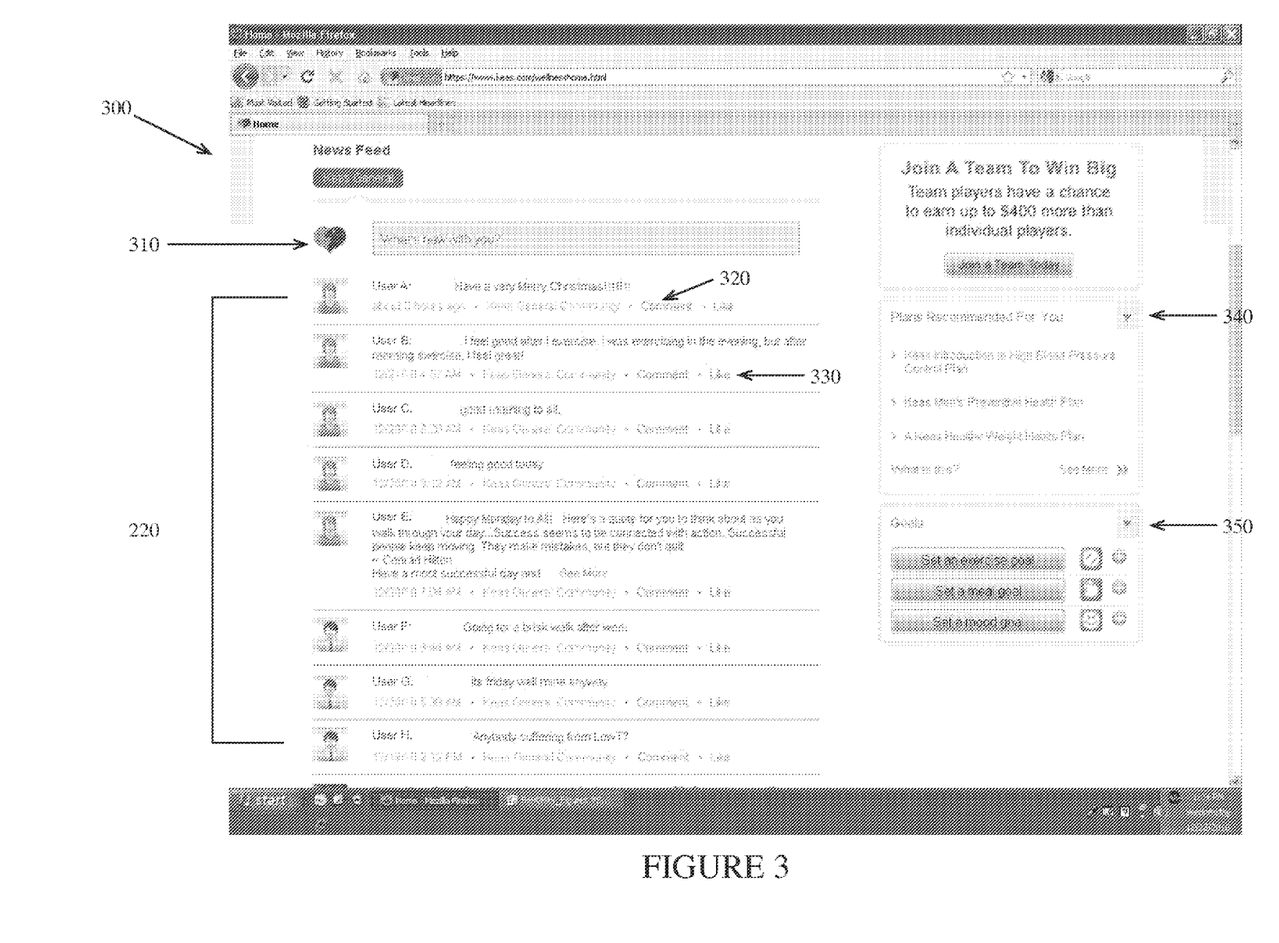
FIG. 3 illustrates an interface for user interaction with other users or team members in a social network.

FIG. 3 illustrates an interface for user interaction with other users or team members in a social network. Interface 300 includes "News feed" 220 which includes status input section 310, "Comment" button 320, "Like" button 330, recommended plans 340, and Goals 350. A user 110A may also subscribe to or follow recommended, personalized health plans. Recommended plans 340 is discussed in more detail in FIG. 6 below.

Status input section 310 may allow a user to input and share information with other users in the same social network or community. The interface for user interaction illustrated in FIG. 3 may allow one user to communicate or provide feedback. User 110A may also interact with other users of the social network at any time, for example, by selecting the "Comment" button 320 or "Like" button 330. For example, in FIG. 3, User B may select the "Comment" button 320 and post a comment in reply to the "Have a very Merry Christmas!!!!!!!" message of User A. Similarly, in response to User F's posting "Going for a brisk walk after work," another user may select the "Comment" button associated with User F's posting and provide feedback to User F. The ability to provide feedback to other users in the social network or community is one key method for providing encouragement, coaching, support to fellow users.

FIG. 3 also includes a "Goals" section 350. Besides recommending various health goals to user 110A, the health management application may allow user 110A to customize or manually set a variety of health-related goals.

Figure 4:
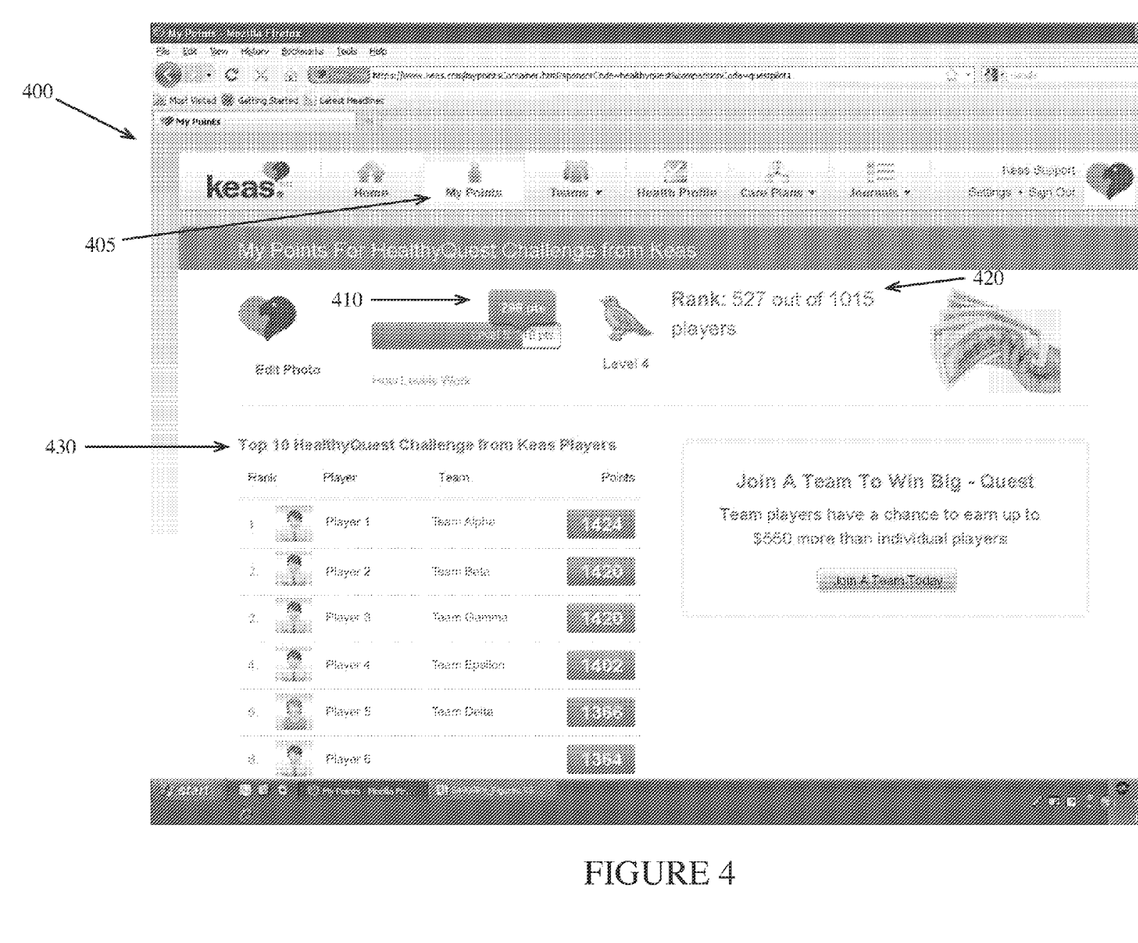
FIG. 4 illustrates an interface for providing points or rewards information.

FIG. 4 illustrates an interface 400 for providing points or rewards information. A user may access interface 400, for example, by selecting the points summary icon 230 shown in FIG. 2. A user of the health management application may earn points or rewards in a variety of ways. Points may be earned, for example, by partially or fully completing a health action or task. A health action or task may be any activity related to the mental or physical health of the user and may promote a healthy lifestyle, diet, or level of physical activity for user 110A. A health action may also include educational or informational tasks such as quizzes, questionnaires, surveys, and games. To earn points, a user may choose from a variety of available health actions, education tasks, or games. In some embodiments, the health management application may provide a personalized action or task following receipt of a request by user 110A. The personalized action may be based on health data previously provided to the health management application by user 110A.

After partial or successful completion of a health action or game, the health management application may award user 110A points or rewards that may be redeemable for an assortment of prizes. Prizes, for example, may include cash prizes, consumer products or electronics, credits redeemable with other websites or business entities, tickets for entry into a lottery or sweepstakes, or the like. FIG. 4 shows interface 400 with the "My Points" menu 405 selected. Interface 400 may include a textual or graphical representation 410 for indicating the current points or rewards accumulated by user 110A. Interface 400 may also include a textual or graphical representation 420 showing the points ranking of the user in relation to other players in the social network of the user or all available players. Interface 400 may also show the top ranking players and total point levels 430.

Figure 5:
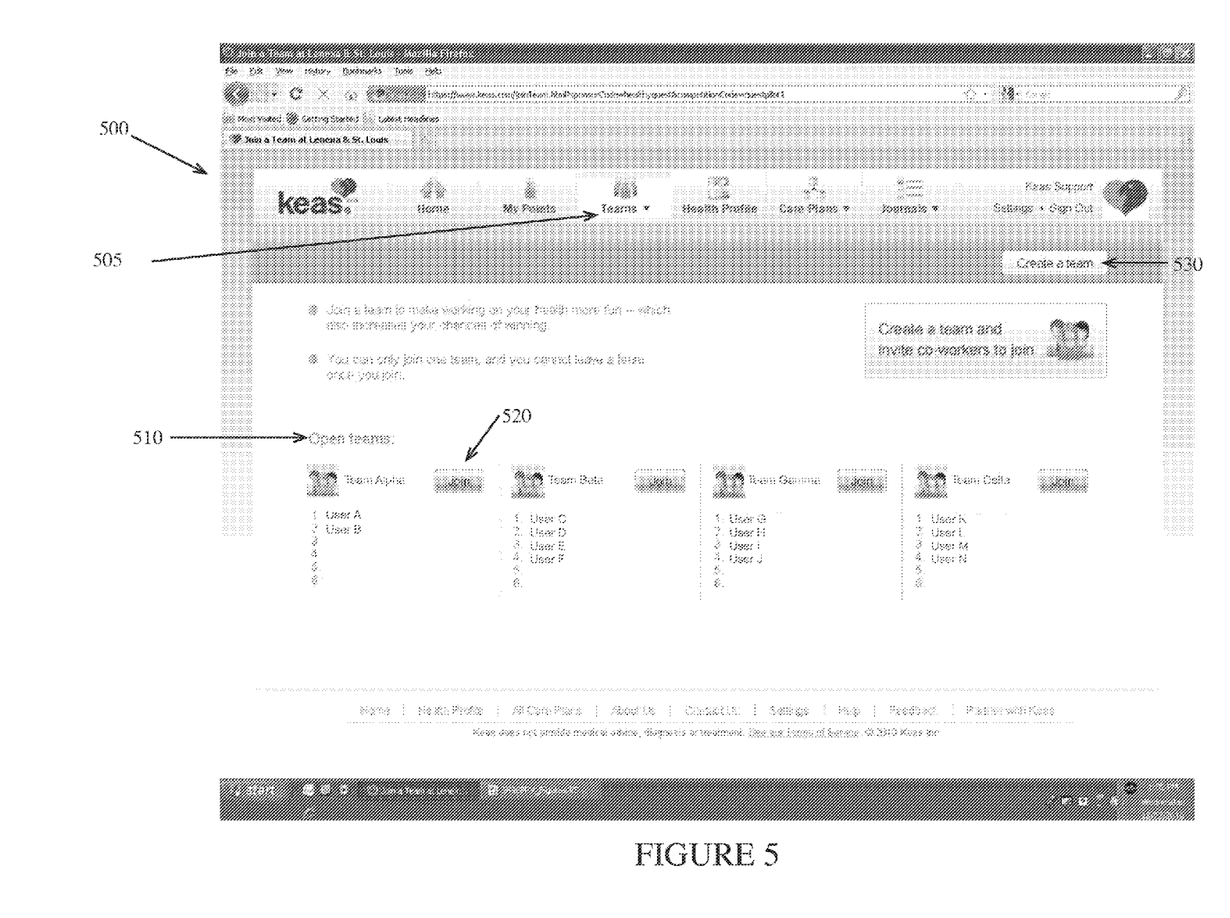
FIG. 5 illustrates an interface for providing team information.

FIG. 5 illustrates an interface 500 for providing team information. User 110A may access interface 500, for example, by selecting the invitation to join a team icon 240 shown in FIG. 2. FIG. 5 shows interface 500 with the "Teams" menu 505 selected. A user of the health management application may choose to work individually or join a team. In a preferred embodiment, team members may share a common health feature, interest, or goal.

The "Teams" menu 505 may show one or more open teams 510 that user 110A may join. In one embodiment, a team is formed using players who are part of the same social network or support group. In another embodiment, a team may include players who are a part of different social networks. A user may join a particular team by selecting the "Join" button 520. User 110A may also start a new team by selecting the "Create a Team" button 530. Each team may be identifiable by a unique name chosen by one or more of the team members.

By joining a team, the points earned by each member may be added together to form a total points score for the team. Teams may compete against one another for prizes. One or more team competitions may be held to encourage teams to build up points or reach a particular health goal. Thus, the formation of teams competing against one another not only yields the possibility of earning valuable prizes but also creates and encourages a collaborative team effort to improve health while doing so. Various competition types and styles are possible. A competition, for example, may end when a total team point value has reached a particular threshold or after a certain period of time has elapsed. Similar competitions may be available to individual users or players who have not joined a team.

Figure 6:
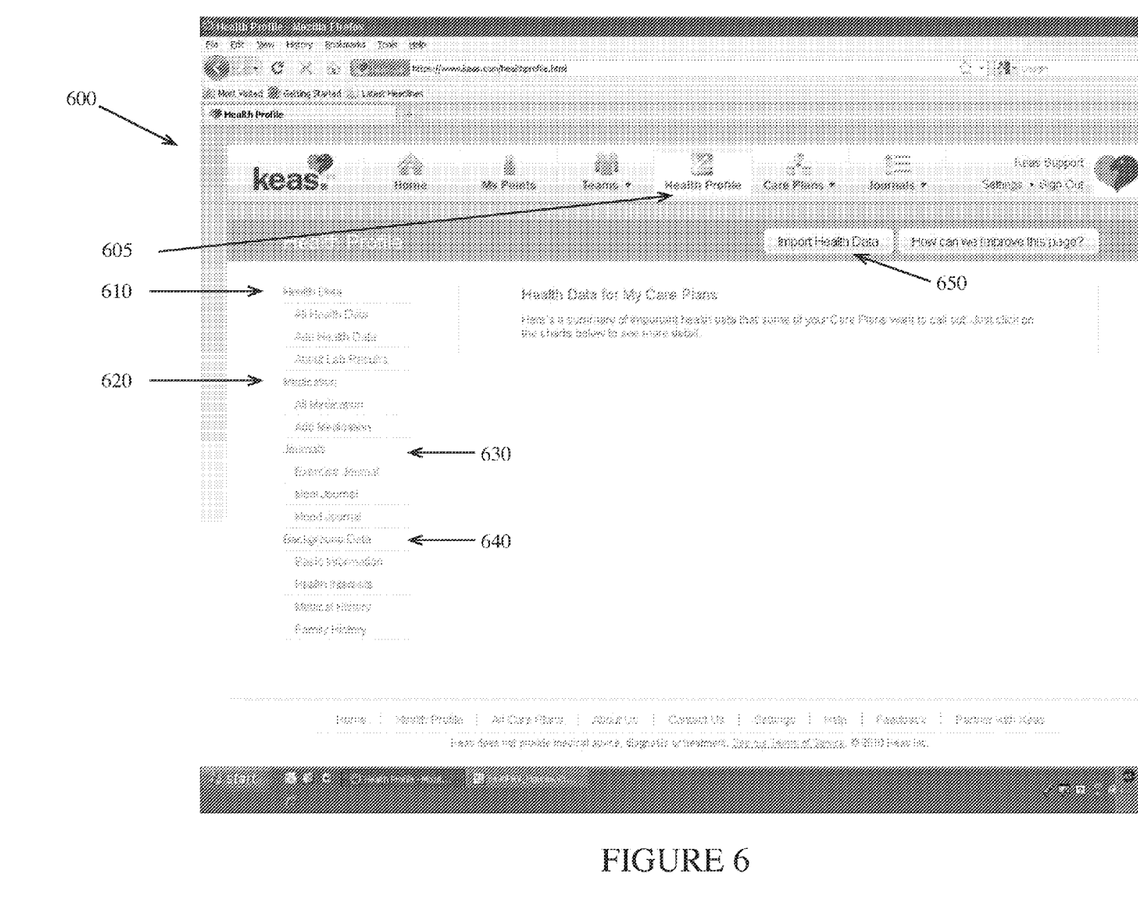
FIG. 6 illustrates an interface showing a user health profile.

FIG. 6 illustrates an interface 600 showing a user health profile. FIG. 6 shows interface 600 with the "Health Profile" menu 605 selected. User 110A may select "Health Data" 610 to view, provide, or update health data. Similarly, user 110A may select "Background Data" 640 to enter or update additional pertinent data such as health interests, medical history, and family history. User 110A may also select "Medication" 620 to add a medication or view or update a list of current medications. Interface 600 also includes "Journals" 630 that allows user 110A to create and maintain periodic (e.g., daily, weekly, monthly, etc.) journals about exercise, meals, or moods. An example of a journal is described in more detail in FIG. 8. User 110A may manually enter data in the health profile or may import existing data by selecting "Import Health Data" 650.

Figure 7:
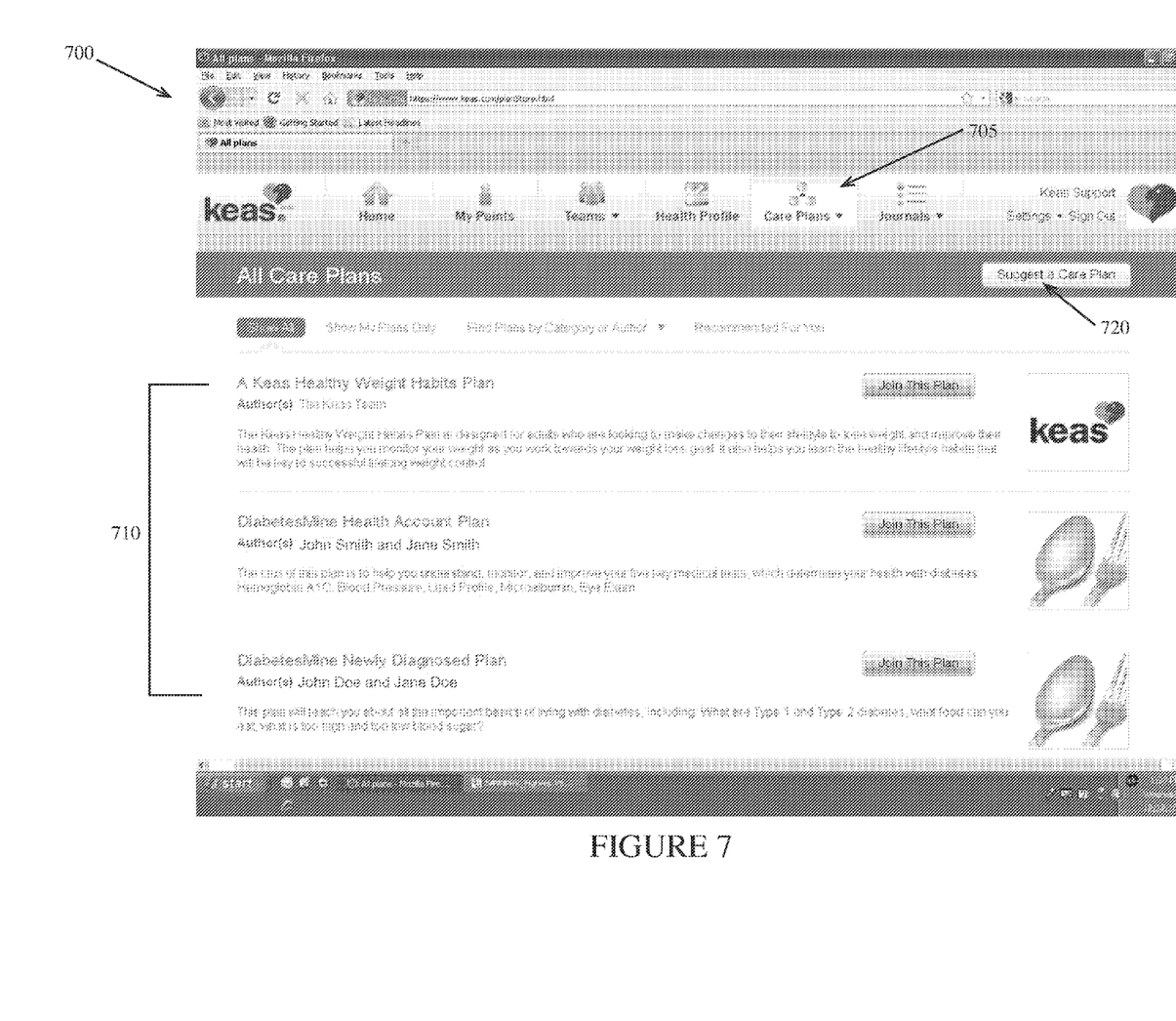
FIG. 7 illustrates an interface for viewing and selecting a care plan.

FIG. 7 illustrates an interface for viewing and selecting a care plan. FIG. 7 shows interface 700 with the "Care Plans" menu 705 selected. In addition to participating in the social network, a user may join a care plan. Interface 700 may display available care plans 710 for user selection. A care plan may include any health regimen, routine, schedule, treatment, or course of therapy that user 110A may review and follow for improved health. A care plan may or may not be directed to a particular health condition or ailment. The health management application may suggest, recommend, or tailor a care plan to a user. The available care plans 710 in interface 700, for example, show care plans directed to healthy weight habits or diabetes. User 110A may also suggest or request a new care plan by selecting "Suggest a Care Plan" 720.

Figure 8:
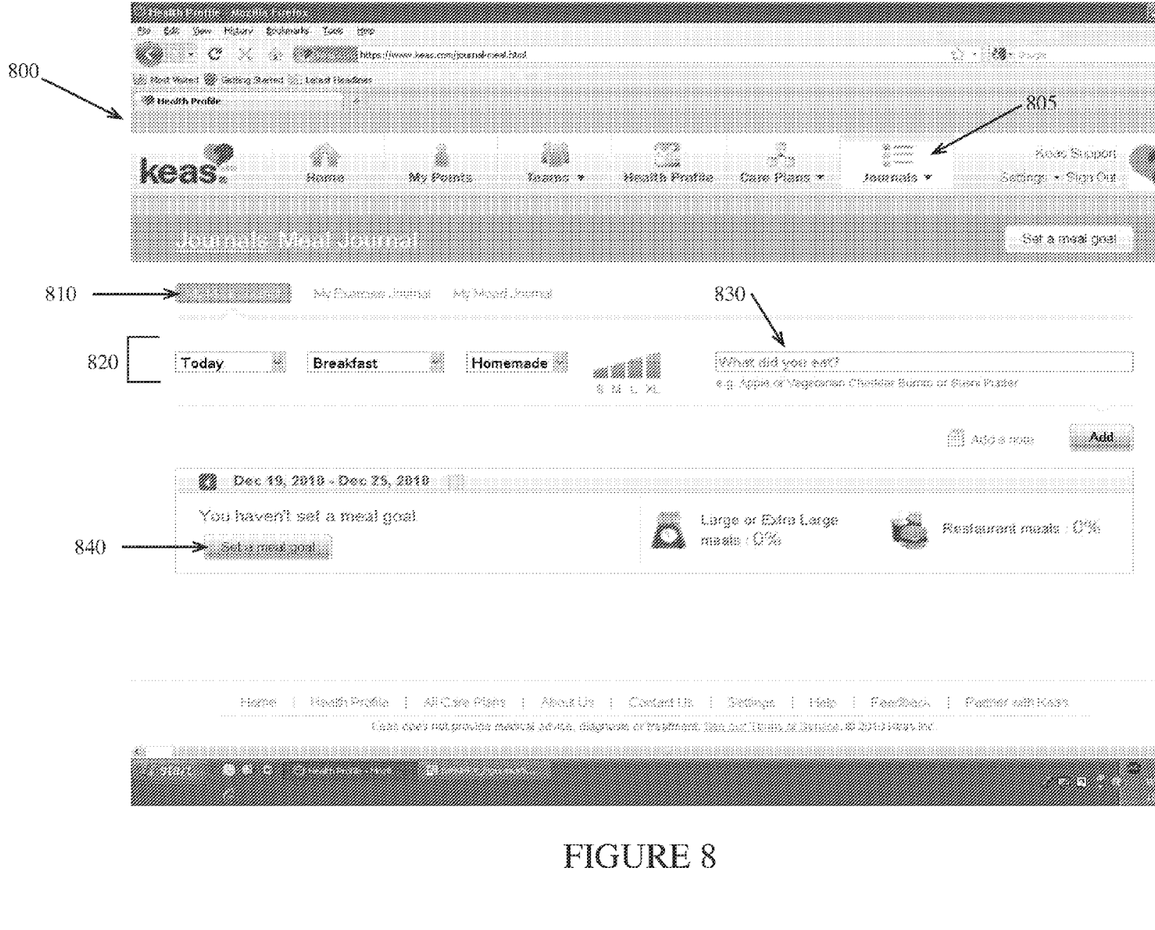
FIG. 8 illustrates an interface for creating and managing a journal.

FIG. 8 illustrates an interface for creating and managing a journal. FIG. 8 shows interface 800 with the "Journals" menu 805 selected. As discussed in FIG. 8, user 110A may create, maintain, and manage one or more journals related to, for example, diet and nutrition, exercise, or moods. Interface 800 shows a meal journal 810. Interface 800 may include one or more drop-down menus 820 for data entry and identification. User 110A, for example, may indicate numerous details about a meal such as meal contents, the date, the type of meal, whether the meal was homemade or pre-made, and the size of the meal. User 110A may also enter data (i.e., details about a meal) in text box 830. User 110A may also have the option to set a meal goal and/or different parameters about diet and nutrition by selecting "Set a meal goal" 840.

Figure 9:
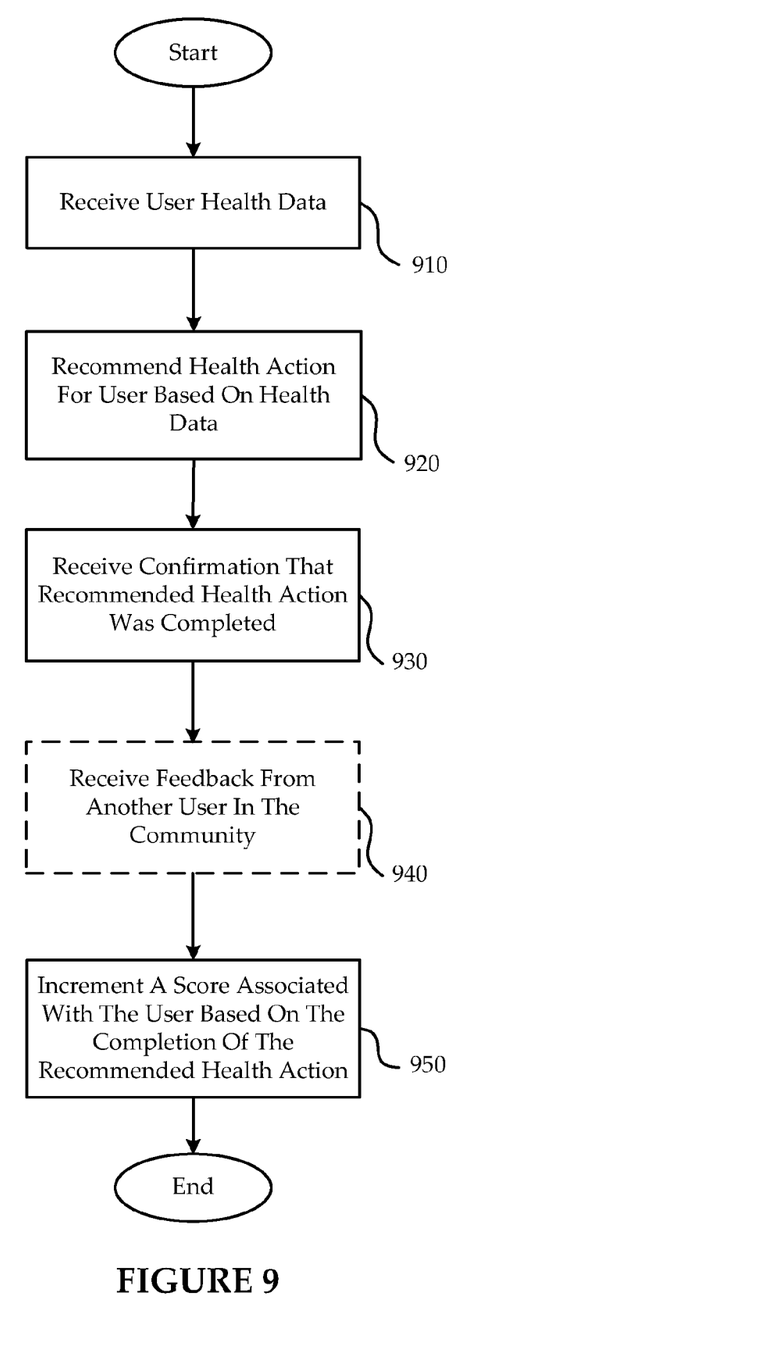
FIG. 9 illustrates a method for health management.

FIG. 9 illustrates a method 900 for health management. The steps identified in FIG. 9 (and the order thereof) are exemplary and may include various alternatives, equivalents, or derivations thereof including but not limited to the order of execution of the same. The steps of the method of FIG. 9 (and its various alternatives) may be embodied in hardware or software including a computer-readable storage medium (e.g., optical disc, memory card, etc.) comprising instructions executable by a processor of a computing device.

At step 910, the health action engine 136 hosted by application server 130 receives health data from a user of the health management application At step 920, the health action engine recommends a health action for the user to complete based on previously provided health data. If no health data has been provided, health action engine 136 may recommend a health action based on the general profile (e.g., basic information) of the user. A health action, for example, may include a physical activity, an activity related to diet/nutrition, a game, or an informational task such as a quiz or questionnaire.

At step 930, the application server 130 may receive confirmation that the recommended health action was partially or successfully completed by the user. At optional step 940, the user may receive feedback from another user in the community. Such feedback may include encouragement, support, or praise for the user. For example, the feedback may encourage the user to complete the recommended health action.

At step 950, the application server 130 (i.e., the score module 140) increments a score associated with the user based on the completion of the recommended health action. A score may be incremented following partial or successful completion of the health action.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

While the present invention has been described in connection with a series of preferred embodiments, these descriptions are not intended to limit the scope of the invention to the particular forms set forth herein. To the contrary, the present descriptions are intended to cover such alternatives, modifications, and equivalents as may be included within the spirit and scope of the invention as defined by the appended claim and otherwise appreciated by one of ordinary skill in the art.

What is claimed is:

1. A method for health management, the method comprising:
 receiving health data from a first user, wherein the first user is a part of a community of users within a social network; and
 executing instructions stored in memory, wherein execution of the instructions by a processor:
  recommends a health action to the first user based on the received health data, increments a score associated with the first user in response to receiving confirmation that the recommended health action was at least partially completed by the first user, decrements a score associated with the first user in response to not receiving confirmation that the recommended health action was at least partially completed by the user after a predetermined period of time has elapsed, calculates a numerical level value associated with the first user based on the score, displays the score, numerical level value, and recommended health action associated with the first user through a social network user interface, the score, numerical level value, and recommended health action being viewable through the social network user interface by a second user in the social network, receives feedback from the second user regarding the score, numerical level value, and recommended health action associated with the first user, the feedback received through comment fields and like buttons within the social network user interface, and displays the feedback from the second user to the first user through the social network user interface.

2. The method of claim 1, wherein the feedback includes encouraging the user to complete the recommended health action.

3. The method of claim 1, wherein execution of the instructions by the processor further recommends a care plan, the care plan including a plurality of personalized health actions.

4. The method of claim 1, wherein execution of the instructions by the processor further recommends a team that the first user may join, the team comprising one or more other users in the social network, the first user and the one or more other users having received one or more common recommended health actions.

5. The method of claim 1, wherein the first user is an anonymous user.

6. The method of claim 1, wherein execution of the instructions by the processor further sends reminders to the first user through the social network user interface to complete the recommended health action.

7. The method of claim 1, wherein execution of the instructions by the processor further receives a plurality of personalized health goals from the first user through the social network user interface.

8. The method of claim 1, wherein execution of the instructions by the processor further awards the first user a redeemable prize in response to the first user completing the recommended health action.

9. The method of claim 1, wherein the first user competes against the second user for a redeemable prize based on the score of the first user and a score of the second user.

10. The method of claim 1, wherein execution of the instructions by the processor further receives a dietary journal entry from the first user through a journal menu in the social network user interface, the journal menu including one or more drop-down menus.

11. A non-transitory computer-readable storage medium having embodied thereon a program, the program bring executable by a processor to perform a method for health management, the method comprising:

receiving health data from a first user, wherein the first user is a part of a community of users within a social network;

recommending a health action to the first user based on the received health data;

incrementing a score associated with the first user in response to receiving confirmation that the recommended health action was at least partially completed by the first user;

decrementing a score associated with the first user in response to not receiving confirmation that the recommended health action was at least partially completed by the user after a predetermined period of time has elapsed, calculating a numerical level value associated with the first user based on the score;

displaying the score, numerical level value, and recommended health action associated with the first user through a social network user interface, the score, numerical level value, and recommended health action being viewable through the social network user interface by a second user in the social network;

receiving feedback from the second user regarding the score, numerical level value, and recommended health action associated with the first user, the feedback received through comment fields and like buttons within the social network user interface; and displaying the feedback from the second user to the first user through the social network user interface.

12. A health management system, comprising:

a processor;

memory; and an application stored in memory and executable by the processor to:

receive health data from a first user, wherein the first user is a part of a community of users within a social network, recommend a health action to the first user based on the received health data, increment a score associated with the first user in response to receiving confirmation that the recommended health action was at least partially completed by the first user, decrement a score associated with the first user in response to not receiving confirmation that the recommended health action was at least partially completed by the user after a predetermined period of time has elapsed, calculate a numerical level value associated with the first user based on the score, display the score, numerical level value, and recommended health action associated with the first user through a social network user interface, the score, numerical level value, and recommended health action being viewable through the social network user interface by a second user in the social network, receive feedback from the second user regarding the score, numerical level value, and recommended health action associated with the first user, the feedback received through comment fields and like buttons within the social network user interface, and display the feedback from the second user to the first user through the social network user interface.

13. The system of claim 12, wherein the application is further executable by the processor to recommend a care plan, the care plan including a plurality of personalized health actions.

14. The system of claim 12, wherein the application is further executable by the processor to recommend a team that the first user may join, the team comprising one or more other users in the social network, the first user and the one or more other users having received one or more common recommended health actions.

15. The system of claim 12, wherein the first user is an anonymous user.

16. The system of claim 12, wherein the application is further executable by the processor to send reminders to the first user through the social network user interface to complete the recommended health action.

17. The system of claim 12, wherein the application is further executable by the processor to receive a plurality of personalized health goals from the first user through the social network user interface.

18. The system of claim 12, wherein the application is further executable by the processor to award the first user a redeemable prize in response to the first user completing the recommended health action.

19. The system of claim 12, wherein the first user competes against the second user for a redeemable prize based on the score of the first user and a score of the second user.

20. The system of claim 12, wherein the application is further executable by the processor to receive a dietary journal entry from the first user through a journal menu in the social network user interface, the journal menu including one or more drop-down menus.

* * * * *